(12) United States Patent
Ichiki et al.

(10) Patent No.: US 9,844,764 B2
(45) Date of Patent: Dec. 19, 2017

(54) PROTEIN OR PEPTIDE PRINTING METHOD, PROTEIN ARRAY OR PEPTIDE ARRAY, AND FUNCTIONAL PROTEIN OR FUNCTIONAL PEPTIDE IDENTIFICATION METHOD

(71) Applicants: THE UNIVERSITY OF TOKYO, Tokyo (JP); NIKON CORPORATION, Tokyo (JP)

(72) Inventors: Takanori Ichiki, Tokyo (JP); Manish Biyani, Tokyo (JP); Hirofumi Shiono, Tokyo (JP)

(73) Assignees: University of Tokyo, Tokyo (JP); Nikon Corporation, Tokyo (JP)

( * ) Notice: Subject to any disclaimer, the term of this patent is extended or adjusted under 35 U.S.C. 154(b) by 569 days.

(21) Appl. No.: 13/772,835

(22) Filed: Feb. 21, 2013

(65) Prior Publication Data

US 2013/0237430 A1 Sep. 12, 2013

Related U.S. Application Data

(63) Continuation of application No. PCT/JP2011/069210, filed on Aug. 25, 2011.

(30) Foreign Application Priority Data

Aug. 27, 2010 (JP) .................................. 2010-191060
Nov. 18, 2010 (JP) .................................. 2010-258302

(51) Int. Cl.
*B01J 19/00* (2006.01)
*G01N 33/68* (2006.01)
(Continued)

(52) U.S. Cl.
CPC .......... *B01J 19/0046* (2013.01); *C07K 17/14* (2013.01); *C12P 21/02* (2013.01);
(Continued)

(58) Field of Classification Search
CPC . B01J 19/0046; G01N 33/6803; C07K 17/14; C07K 2319/21; C12P 21/02
See application file for complete search history.

(56) References Cited

U.S. PATENT DOCUMENTS

2004/0161748 A1  8/2004  He et al.
2008/0312103 A1* 12/2008  Nemoto ............. C12N 15/1062
                                                506/17
(Continued)

FOREIGN PATENT DOCUMENTS

EP    2 090 888 A1   8/2009
JP    A-2002-253240  9/2002
(Continued)

OTHER PUBLICATIONS

NEB (PURExpress™ In Vitro Protein Synthesis Kit instruction manual from May 2009).*

(Continued)

*Primary Examiner* — Jeremy C Flinders
(74) *Attorney, Agent, or Firm* — Finnegan, Henderson, Farabow, Garrett & Dunner, LLP

(57) ABSTRACT

The present invention relates to a protein or peptide printing method, comprising (a) a step for preparing nucleic acids and a cell-free protein synthesis system in an engraved plate composed of microscopic grooves having a specific opening shape, (b) a step for superimposing a substrate on the engraved plate so as to contact a protein or peptide to be synthesized in the microscopic grooves, and (c) a step for synthesizing the protein or peptide from the nucleic acids using the cell-free protein synthesis system in the microscopic grooves, and immobilizing the protein or peptide on the substrate along the specific opening shapes of the microscopic grooves.

10 Claims, 8 Drawing Sheets

(51) Int. Cl.
*C07K 17/14* (2006.01)
*C12P 21/02* (2006.01)
*C40B 20/02* (2006.01)

(52) U.S. Cl.
CPC ..... *G01N 33/6803* (2013.01); *C07K 2319/21* (2013.01); *C40B 20/02* (2013.01)

(56) References Cited

U.S. PATENT DOCUMENTS

| | | | |
|---|---|---|---|
| 2010/0035769 | A1 | 2/2010 | Nemoto et al. |
| 2012/0015844 | A1* | 1/2012 | Zengerle ............ C12Q 1/6837 506/9 |

FOREIGN PATENT DOCUMENTS

| | | |
|---|---|---|
| JP | 2004-506898 | 3/2004 |
| JP | 2008-116218 | 5/2008 |
| WO | WO 02/14860 A1 | 2/2002 |
| WO | WO 2008/053598 A1 | 5/2008 |

OTHER PUBLICATIONS

Biyani et al. (Nucleic Acids Research, 2006, 34(20):e140 pp. 1-9).*
Lagally et al. (Anal.Chem., 2001, 73:565-570).*
Second Examination Report issued by Chinese Patent Office in Chinese patent application No. 201180041500.4, dated Jul. 7, 2014, 17 pages.
Third Examination Report issued by Chinese Patent Office in Chinese patent application No. 201180041500.4, dated Nov. 14, 2014, 17 pages.
The Rejection Decision issued by the State Intellectual Property Office of the People's Republic of China in counterpart Chinese Application No. 201180041500.4, dated May 6, 2015, 20 pages.
First Examination Report issued by Chinese Patent Office in Chinese patent application No. 201180041500, dated Feb. 21, 2014, 14 pages.
C.D. James, et al., "Patterned Protein Layers on Solid Substrates by Thin Stamp Microcontact Printing", Langmuir, vol. 14, pp. 741-744 (1998).
Mingyue He, et al., "In situ synthesis of protein arrays", Biotechnology, vol. 19, No. 1, pp. 4-9 (2006).
Manish Biyani, et al., "Microintaglio Printing of Biomolecules and its Application to in situ Production of Messenger Ribonucleic Acid Display Microarray", Applied Physics Express, vol. 4, No. 4. pp. 047001-047003 (2011).
Mingyue He, et al., "Printing protein arrays from DNA arrays", Nature Methods, vol. 5, No. 2, pp. 175-177 (Feb. 2008).
Written Opinion of the International Searching Authority issued by the Japanese Patent Office in corresponding International Application No. PCT/JP2011/069210, dated Nov. 29, 2011 (7 pages).
International Search Report issued by the Japanese Patent Office in corresponding International Application No. PCT/JP2011/069210, dated Nov. 29, 2011 (4 pages).
Office Action issued by Japanese Patent Office in counterpart Application No. 2012-530714 dated Aug. 25, 2015, and English translation thereof.
Re-examination Notification issued by the State Intellectual Property Office of the People's Republic of China in counterpart Application No. 201180041500.4 dated Aug. 8, 2016, and English translation thereof.
Reexamination Decision issued by the State Intellectual Property Office of the People's Republic of China in counterpart Application No. 201180041500.4 dated Oct. 24, 2016, and English translation thereof.

* cited by examiner

PROTEIN OR PEPTIDE PRINTING METHOD, PROTEIN ARRAY OR PEPTIDE ARRAY, AND FUNCTIONAL PROTEIN OR FUNCTIONAL PEPTIDE IDENTIFICATION METHOD

TECHNICAL FIELD

The present invention relates to a protein or peptide printing method, an array produced according to these methods, and a functional protein or functional peptide identification method that uses that array. The present application claims priority on the basis of Japanese Patent Application No. 2010-191060, filed in Japan on Aug. 27, 2010, and Japanese Patent Application No. 2010-258302, filed in Japan on Nov. 18, 2010, the contents of which are incorporated herein by reference.

BACKGROUND ART

In recent years, methods for patterning molecules on a substrate have come to be used in various biological fields such as biochips or biosensors.

Attention is particularly focusing on the microcontact printing (to be referred to as μCP) method that enables patterning over large surfaces on the submicron order. This μCP method is applied to patterning of proteins and other biomolecules since it does not require strong acid or strong base as required by photolithographic patterning.

However, since proteins and other biomolecules are susceptible to denaturation and decomposition, various modifications have been made to the aforementioned μCP method (see, for example, Non-Patent Document 1).

In the method proposed in Non-Patent Document 1, silicone rubber used for printing is subjected to low-temperature plasma treatment to increase the hydrophilicity of the silicone rubber surface. As a result, denaturation and the like of proteins and other biomolecules are decreased.

PRIOR ART DOCUMENTS

Non-Patent Documents

Non-Patent Document 1: James, et al., Langmuir, Vol. 14, pp. 741-744, 1998

DISCLOSURE OF THE INVENTION

Problems to be Solved by the Invention

However, since the method proposed in Non-Patent Document 1 uses relief printing technology and proteins and other biomolecules are printed directly, the protein used as ink dries easily, thereby leaving room for improvement in terms of being able to print proteins having low storage stability, for example.

With the foregoing in view, an object of the present invention is to provide a protein or peptide printing method capable of reducing damage imparted to protein or peptide having low storage stability and printing the aforementioned protein or peptide in an arbitrary shape, an array produced according to these methods, and a functional protein or functional peptide identification method that uses the array.

Means for Solving the Problems

As a result of conducting extensive studies to solve the aforementioned problems, the inventors of the present invention found that the problems can be solved by applying intaglio printing technology.

Namely, an embodiment of the present invention provides the inventions described in (1) to (12) below.

(1) A protein or peptide printing method in one embodiment of the present invention comprises: (a) a step for preparing nucleic acids and an acellular protein synthesis system (a cell-free protein synthesis system) in an engraved plate (a microintaglio plate) composed of microscopic grooves having a specific opening shape, (b) a step for superimposing a substrate on the engraved plate so as to contact a protein or peptide to be synthesized in the microscopic grooves, and (c) a step for synthesizing the protein or peptide from the nucleic acids using the acellular protein synthesis system in the microscopic grooves, and immobilizing the protein or peptide on the substrate along the specific opening shapes of the microscopic grooves.

(2) In the protein or peptide printing method in one embodiment of the present invention, the protein or peptide preferably includes an amino acid sequence as a solid-phase binding site, and the substrate preferably has a solid-phase binding site recognition site having affinity for the amino acid sequence.

(3) In the protein or peptide printing method in one embodiment of the present invention, the solid-phase binding site recognition site is preferably nickel ion or cobalt ion.

(4) In the protein or peptide printing method in one embodiment of the present invention, the amino acid sequence is preferably polyhistidine.

(5) The protein or peptide printing method in one embodiment of the present invention comprises: (a) a step for preparing nucleic acids, a biotinylated puromycin derivative and an acellular protein synthesis system in an engraved plate composed of microscopic grooves having a specific opening shape, (b) a step for superimposing an avidin-labeled substrate on the engraved plate so as to contact a protein or peptide to be synthesized in the microscopic grooves, and (c) a step for synthesizing a protein or peptide from the nucleic acids using the acellular protein synthesis system in the microscopic grooves, and immobilizing the protein or peptide on the substrate along the specific opening shapes of the microscopic grooves.

(6) In the protein or peptide printing method in one embodiment of the present invention, the biotinylated puromycin derivative is preferably a compound represented by the following general formula (1):

[Chemical Formula 1]

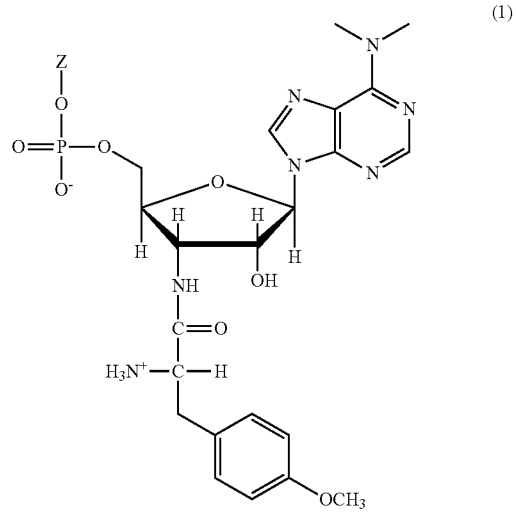

(wherein, Z represents a group represented by the following formula (2), (3) or (4):

[Chemical Formula 2]

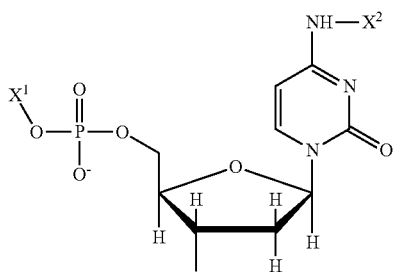

(2)

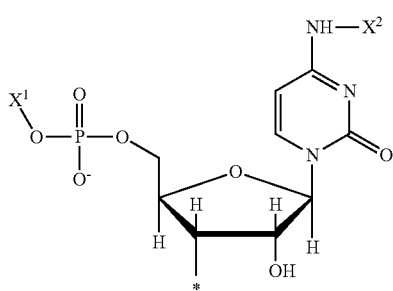

(3)

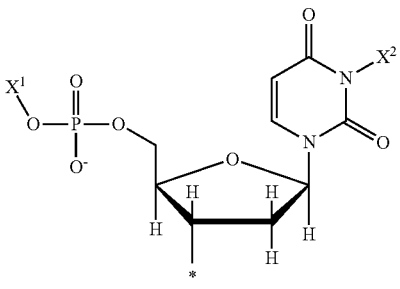

(4)

(wherein, at least one of $X^1$ and $X^2$ represents a group represented by the following formula (5), and the other is a fluorescent group or hydrogen atom, and * represents a binding site:

[Chemical Formula 3]

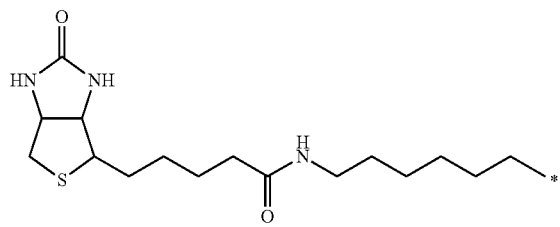

(5)

(wherein, * represents a binding site))).

(7) In the protein or peptide printing method in one embodiment of the present invention, Z is preferably a group represented by the formula (2).

(8) In the protein or peptide printing method in one embodiment of the present invention, the acellular protein synthesis system preferably consists of independently purified factors required for protein synthesis.

(9) In the protein or peptide printing method in one embodiment of the present invention, in the step (a), the nucleic acids are preferably DNA that have been labeled at their solid-phase binding sites, and are immobilized by magnetic beads that have been labeled at their solid-phase binding site recognition sites.

(10) In the protein or peptide printing method in one embodiment of the present invention, in the step (a), the nucleic acids are preferably DNA that have been labeled with biotin, and are preferably immobilized by magnetic beads that have been labeled with streptavidin.

(11) A protein array or peptide array in one embodiment of the present invention is produced using the aforementioned protein or peptide printing method.

(12) A functional protein or functional peptide identification method in one embodiment of the present invention comprises: carrying out functional screening using the protein array or peptide array, and identifying a protein or peptide that has been specified by the functional screening and immobilized in the step (c) by using nucleic acids in the corresponding microscopic grooves in the step (a).

Effects of the Invention

According to the protein or peptide printing method of the present invention, a protein array or peptide array is obtained in which the protein or peptide is printed in an arbitrary shape without imparting damage to protein or peptide having low storage stability.

According to the present invention, the protein array or peptide array can be made to have high density, and since this high-density protein array or high-density peptide array is not only immobilized with numerous types of proteins or peptides, but also is immobilized with a large number of protein or peptide molecules per spot, it has high usage value.

In addition, since the functional protein or functional peptide identification method of the present invention is able to rapidly identify a protein or peptide having a desired function in a high-density protein array or peptide array, it can be preferably used in molecular evolution engineering applications.

BEST MODE FOR CARRYING OUT THE INVENTION

Protein or Peptide Printing Method

First Embodiment

Figure 1A:
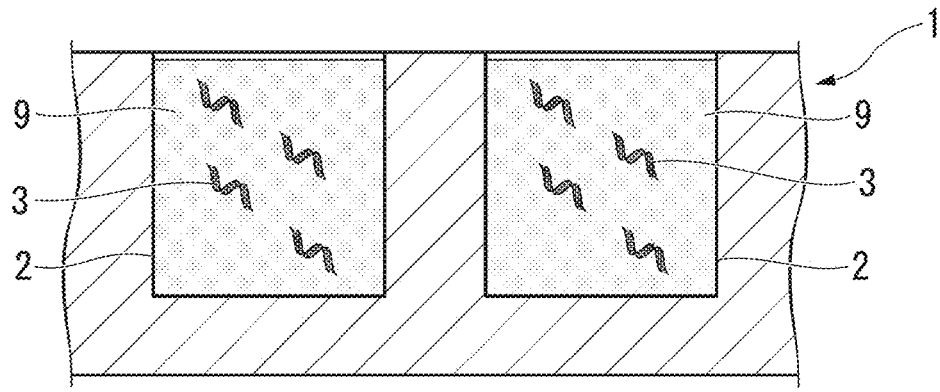
FIG. 1A is a schematic diagram of a protein or peptide printing method in the present embodiment.
Figure 1B:
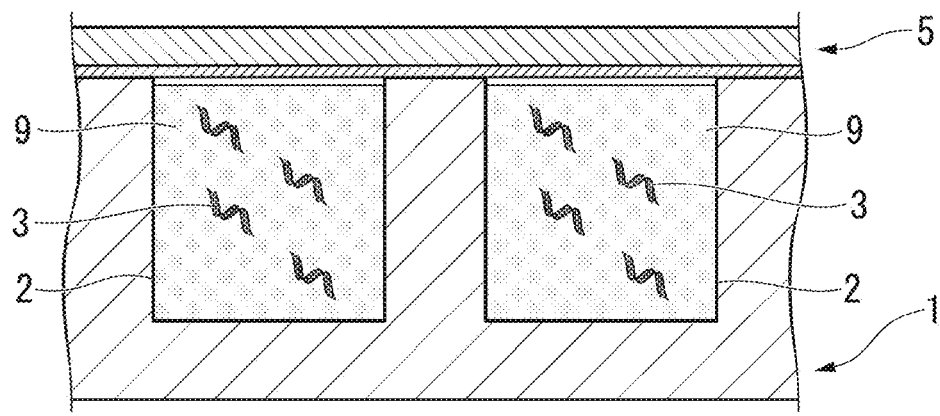
FIG. 1B is a schematic diagram of a protein or peptide printing method in the present embodiment.
Figure 1C:
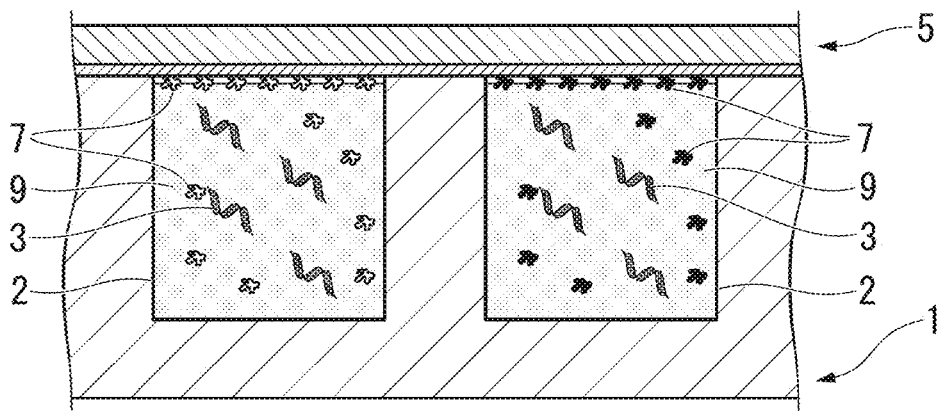
FIG. 1C is a schematic diagram of a protein or peptide printing method in the present embodiment.
Figure 2A:
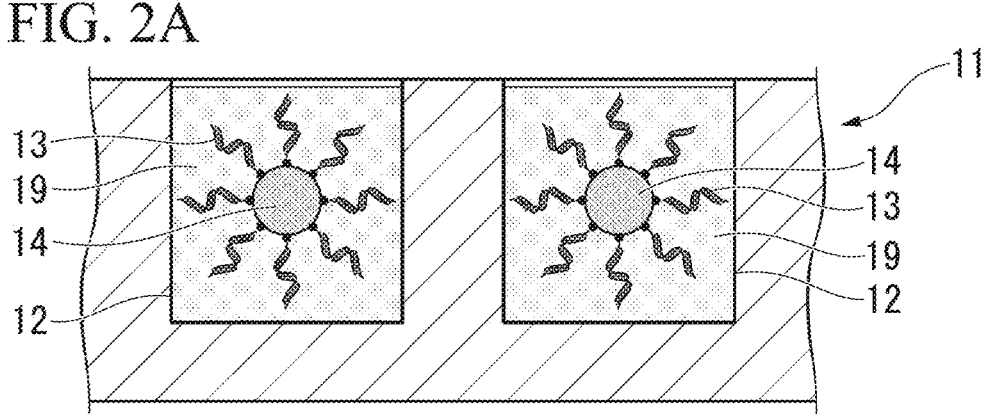
FIG. 2A is a schematic diagram of a protein or peptide printing method in the present embodiment.
Figure 2B:
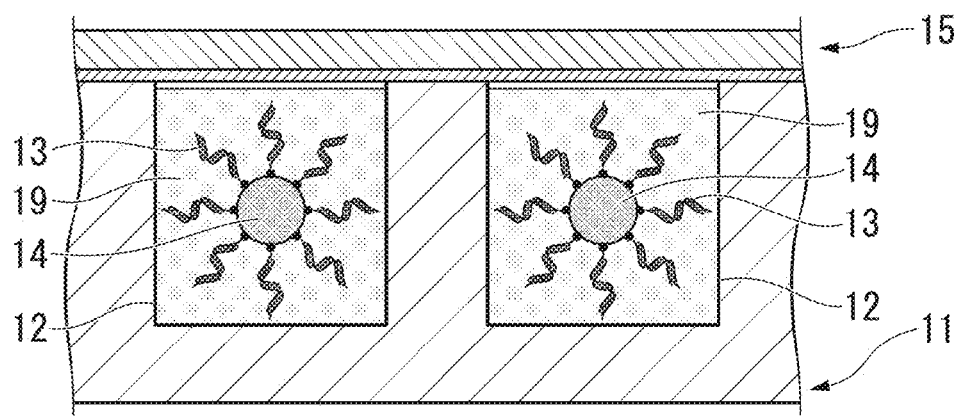
FIG. 2B is a schematic diagram of a protein or peptide printing method in the present embodiment.
Figure 2C:
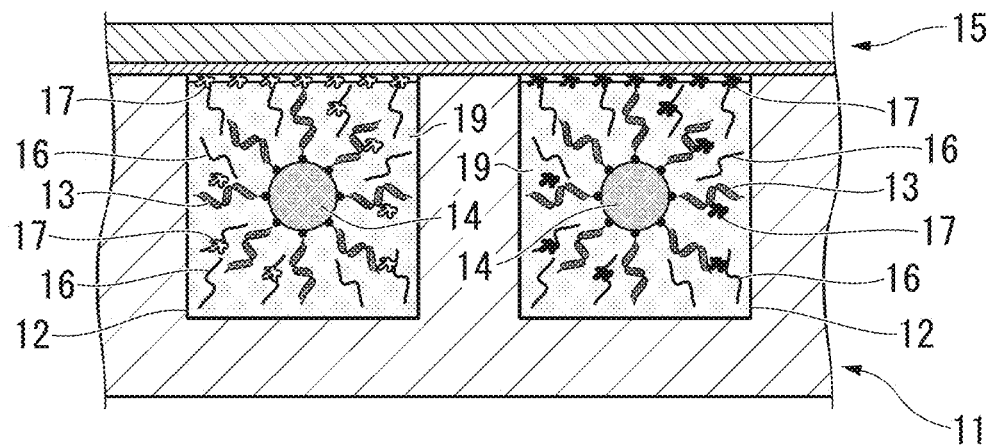
FIG. 2C is a schematic diagram of a protein or peptide printing method in the present embodiment.
Figure 2D:
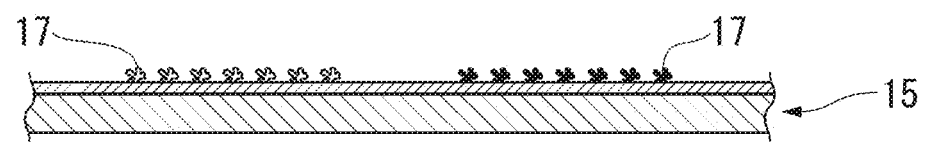
FIG. 2D is a schematic diagram of a protein or peptide printing method in the present embodiment.
Figure 2E:
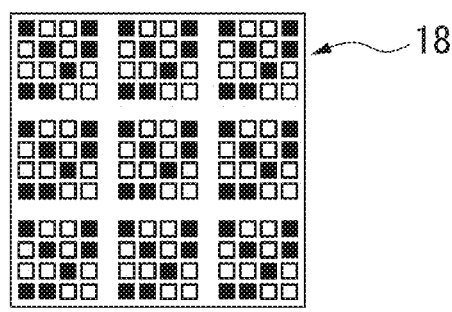
FIG. 2E is a schematic diagram of a protein or peptide printing method in the present embodiment.

As shown in FIGS. 1A to 1C, the protein or peptide printing method of the present embodiment comprises:

(a) a step for preparing nucleic acids 3 and an acellular protein synthesis system (a cell-free protein synthesis system) 9 in an engraved plate (a microintaglio plate) 1 composed of microscopic grooves 2 having a specific opening shape, (b) a step for superimposing a substrate 5 on the engraved plate 1 so as to contact a protein or peptide 7 to be synthesized in the microscopic grooves 2, and (c) a step for synthesizing the protein or peptide 7 from the nucleic acids 3 using the acellular protein synthesis system 9 in the microscopic grooves 2, and immobilizing the protein or peptide 7 on the substrate 5 along the specific opening shapes of the microscopic grooves 2.

The following provides an explanation of each step with reference to FIGS. 2A to 2E.

Step (a) is a step for preparing nucleic acids and an acellular protein synthesis system 19 in the microscopic grooves 12 in an engraved plate 11 composed of the aforementioned microscopic grooves 12 having a specific opening shape.

The aforementioned engraved plate 11 preferably consists of a plurality of the microscopic grooves 12. In the present embodiment, since the engraved plate 11 used consists of the microscopic grooves 12 having individual walls, when printing a protein or peptide 17 onto a substrate 15, there is no concern over leakage and the like between each spot, a pattern of a fine shape can be printed, and in the step (c) to be subsequently described, the specific opening shape possessed by the aforementioned microscopic grooves 12 is printed as is onto the substrate 15 and is reflected in the shape of the spots.

Accordingly, a high-density protein array 18 can be produced according to this shape. Moreover, since the shape of the spots on the substrate 15 is dependent on the opening shape of the aforementioned microscopic grooves 12, in the present embodiment, the shape of the spots on the substrate 15 can be determined to have an arbitrary shape.

In addition, in contrast to there being restrictions on the number of DNA molecules able to be immobilized on a DNA microarray, in the present embodiment, since a large number of DNA molecules can be added to the engraved plate 11, a large number of protein molecules can be synthesized by using the acellular protein synthesis system to be subsequently described, and a protein array can be produced on which is immobilized a large number of protein molecules per spot. In addition, in the present embodiment, since the engraved plate 11 is used that consists of the microscopic grooves 12, a transcription stage and translation stage can be carried out all at once, thereby resulting in greater efficiency.

The surface of the engraved plate 11 and the inner walls of the microscopic grooves 12 can be preferably coated with a blocking agent for preventing non-specific adsorption of DNA and other biomolecules, examples of which include polyethylene glycol (PEG) or 2-methacryloyloxyethyl phosphorylcholine (MPC). As a result of coating with this blocking agent, non-specific adsorption of biomolecules to a substrate surface or microreaction vessel (microreactor) can be inhibited.

The substrate material used for the engraved plate 11 is preferably a transparent glass or polymer, and for the purpose of inhibiting leakage, is more preferably an elastomer material such as polydimethylsiloxane. Furthermore, in the case of using an elastomer material for the substrate material used for the engraved plate 11, there is the advantage of local deformation of the elastomer making it possible to avoid detrimental effects on adhesion between the entire intaglio plate and the substrate 15 that occur when microscopic debris and other particles are trapped between the intaglio plate and the substrate 15.

In step (a), although there are no particular limitations on the nucleic acids prepared in the microscopic grooves 12 provided they encode a protein or peptide used in printing, DNA or mRNA is preferable, and DNA is more preferable from the viewpoint of handling ease.

The DNA is preferably immobilized on the engraved plate 11 from the viewpoint of the need to specify positional information on the engraved plate 11 of the DNA.

In addition to methods using avidin-biotin binding, methods such as those utilizing DNA labeled with a functional group such as an amino group, aldehyde group or SH group and a solid phase surface-treated with a silane coupling agent having an amino group, aldehyde group or epoxy group and the like can also be used, and a method using avidin-biotin binding is particularly preferable. In this case, avidin is preferably immobilized on the solid phase while biotin is preferably bound to the DNA.

The aforementioned solid phase preferably consists of beads from the viewpoint of subsequent recovery of DNA, and magnetic beads are more preferable from the viewpoint of being able to be arranged in each of the microscopic grooves 12 of the engraved plate 11 in a short period of time.

In addition, in the case of using beads, a larger number of DNA molecules can be immobilized on the substrate in the case of immobilizing DNA. Since the number of DNA molecules is reflected in the number of protein molecules produced using the acellular protein synthesis system, according to the present embodiment, a larger number of protein molecules can be immobilized per spot than methods consisting of manufacturing a protein array from a DNA microarray.

In the present embodiment, in the case of using magnetic beads for the solid phase, a magnetic plate is preferably arranged beneath the substrate material used for the engraved plate 11.

As a result of using the engraved plate 11 employing such a structure, magnetic beads 14 can be easily and reliably arranged in the microscopic grooves 12. More specifically, a magnet is arranged beneath the substrate material, and a dispersion of the magnetic beads 14 with DNA 13 immobilized thereon is dropped onto the substrate material. Due to the magnetic action of the magnetic beads 14 and a magnetic thin film, the magnetic beads are attracted into the microscopic grooves 12, enabling them to be easily arranged therein. Moreover, by suitably moving the magnet in a planar direction relative to the substrate, the magnetic beads 14 are dispersed, and the filling rate of the magnetic beads 14 in the microscopic grooves 12 improves. The magnetic field strength applied to a substrate for arranging beads with a magnet is preferably 100 gauss to 10,000 gauss in terms of obtaining the desired effect.

In addition, since magnetism of the magnetic plate remains even after the magnet has been removed, the magnetic beads 14 can continue to be held in a stable arrangement.

A metal such as nickel, nickel alloy, iron or iron alloy can be preferably used for the magnetic material, and in the present embodiment, a magnetic material having large residual magnetism is used preferably.

The filling rate of the magnetic beads 14 in the microscopic grooves 12 is dependent on the diameter of the microscopic grooves 12, and since filling rate increases if the diameter of the microscopic grooves 12 is slightly larger than the diameter of the magnetic beads 14, the diameter of the microscopic grooves 12 is preferably 1 to 2 times the diameter of the magnetic beads. In addition, in terms of filling a single magnetic bead 14 into a single microscopic groove 12, the depth of the microscopic grooves 12 is preferably 1 to 2 times the diameter of the magnetic beads 14.

The microscopic grooves 12 are preferably hydrophilic, and subjecting the microscopic beads 12 to hydrophilic treatment by irradiating with oxygen plasma and the like facilitates filling of a liquid in which magnetic beads are dispersed into the microscopic grooves 12, resulting in an improved filling rate.

In the present embodiment, when preparing amino acids in the microscopic grooves 12, a mixture of a plurality of types of DNA as in a DNA library and the like may be mixed with a DNA amplification reagent, and the mixture may be diluted with a suitable buffer and the like, followed by dispensing into the microscopic grooves 12. In addition, a mutant DNA library into which gene mutations have been introduced may also be used as a DNA library preferably used in molecular evolution engineering applications. Here, the DNA is preferably accurately diluted and dispensed so there is a single DNA molecule in each of the microscopic grooves 12. There are no particular limitations on the order in which DNA is mixed with amplification reagent and diluted, and if the conditions of the engraved plate 11 are set and the reaction is carried out so that DNA is applied to amplification after dispensing, different types of DNA can be amplified in each of the microscopic grooves 12.

Here, in the case of amplifying DNA, a PCR reaction is used preferably, and commercially available reaction solutions required for the reaction can be used. In addition, in the case of immobilizing DNA in the microscopic grooves 12 on beads, if an amplification reaction is carried out so that biotin is incorporated in the DNA and beads are used that have been coated with avidin, the DNA can be easily immobilized on the beads through avidin-biotin binding. An example of a method used to incorporate biotin in DNA consists of a method that uses PCR primers labeled with biotin.

Step (b) is a step for superimposing the substrate 15 on the aforementioned engraved plate 11 so that the substrate 15 contacts protein or peptide to be synthesized in the aforementioned microscopic grooves 12.

The aforementioned step (b) utilizes intaglio printing technology in which ink is placed in a concave portion of a plate, and paper and the like is pressed onto the plate from above. The aforementioned step (b) is a step for dropping a reaction solution onto grooves in the form of the microscopic grooves 12 on the engraved plate 11, superimposing the substrate 15 on the aforementioned engraved plate 11 from above, and then pressing on the substrate 15 using a hand press and the like, and in step (c) to be subsequently described, a protein or peptide 17 is printed onto the substrate 15. Accordingly, since the specific opening shape of the microscopic grooves 12 is reflected as is in the shape of the spots on the substrate 15, according to the present embodiment, protein or peptide of an arbitrary size and shape can be printed on the substrate. Thus, if the shape is fine, the shape of the transferred spots is also fine. As a result of having this fine shape, a high-density protein array or peptide array can be fabricated.

Moreover, according to step (c) to be subsequently described, protein or peptide can be synthesized from the amino acids, and the protein or the peptide can be printed on the substrate without altering the positional information of the nucleic acids immobilized on an array.

Although the aforementioned opening shape of the aforementioned microscopic grooves 12 is arbitrary, it is preferably of a shape that allows at least one bead to be filled therein. For example, the aforementioned opening shape of the aforementioned microscopic grooves 12 may be circular, rectangular, hexagonal or linear.

Examples of the substrate 15 used in the aforementioned step (b) include a glass substrate, silicon substrate, polymer substrate and metal substrate.

In the present embodiment, the surface of the substrate 15 superimposed on the engraved plate 11 is not necessarily required to be flat, and for example, may be formed to have surface irregularities in order to increase the surface area on which the protein or peptide 17 is immobilized. However, when superimposing the substrate 15 on the engraved plate 11, the substrate surface of the portion contacted by the engraved plate 11 is required to be flat so that reagent and the like within all of the microscopic grooves 12 on the engraved plate 11 is sealed without leaking.

Step (c) is a step for synthesizing the protein or peptide 17 from the aforementioned nucleic acids using the aforementioned acellular protein synthesis system 19 in the aforementioned microscopic grooves 12, and immobilizing the protein or peptide 17 on the aforementioned substrate 15 along the specific opening shape of the aforementioned microscopic grooves 12.

The acellular protein synthesis system refers to a protein translation system composed of components having the ability to synthesis protein extracted from suitable cells, and this system contains elements required for translation, such as ribosomes, translation initiation factors, translation elongation factors, dissociation factors or aminoacyl tRNA synthetase. Examples of such a protein translation system include *Escherichia coli* extract, rabbit reticulocyte extract and wheat germ extract. Another example is a reconfigurable acellular protein synthesis system (a reconfigurable cell-free protein synthesis system) composed only of factors obtained by independently purifying the aforementioned elements required for translation. Reconfigurable acellular protein synthesis systems are able to enhance translation efficiency since they are able to more easily prevent contamination by nucleases and proteases than in the case of using a conventional cell extract. From the viewpoint of this translation efficiency, a reconfigurable acellular protein synthesis system is preferably used for the acellular protein synthesis system in the present embodiment.

The use of such a system makes it possible to produce the protein or peptide 17 in the aforementioned microscopic grooves 12.

Since synthesized protein is susceptible to deactivation due to decomposition or denaturation, when printing onto a substrate, it is necessary to maintain the protein in as stable a state as possible. In the present embodiment, since the protein 17 synthesized in the microscopic grooves 12 is printed as is on the substrate 15, the array 18 can be fabricated while decreasing protein deactivation as much as possible.

In the aforementioned step (c), in the case the nucleic acids used in the acellular protein synthesis system 19 consist of the DNA 13, a step is included in which mRNA 16 is synthesized from the aforementioned DNA 13 using an acellular protein transcription system (a cell-free protein transcription system). The aforementioned mRNA 16 is obtained from the immobilized DNA 13 that encodes the protein to be screened, by transcribing with RNA polymerase. An example of RNA polymerase is T7 RNA polymerase.

In order to carry out the transcription reaction and a translation reaction to be subsequently described in the optimum state, the reactions may be carried out by combining other apparatuses and the like that control the temperature of the engraved plate 11, pH conditions in the microscopic grooves 12 and the like.

In addition, a system that couples transcription and translation may also be used from the viewpoint of simplicity.

In step (c), the aforementioned protein or peptide is immobilized on the substrate 15 following synthesis of the aforementioned protein or peptide 17. For example, after having added required reagents and materials (nucleic acids) to the microscopic grooves 12 on the engraved plate 11, in step (a), the substrate 15 is used to seal the engraved plate 11 from above in step (b). In step (c), a series of transcription and translation reactions are carried out after mixing the reagents to obtain the mRNA 16 from the DNA 13 and the protein 17 from the mRNA 16, followed by additionally binding a tag having the translated protein 17 to the aforementioned substrate 15.

In the present embodiment, the aforementioned protein or peptide contains a solid-phase binding site in the form of an amino acid sequence in order to immobilize the protein or peptide to the substrate, and the aforementioned substrate has a solid-phase binding site recognition site that has affinity for the aforementioned amino acid sequence.

Examples of this combination of solid-phase binding site and solid-phase binding site recognition site include the combination of maltose-binding protein and maltose, G protein and guanine nucleotide, polyhistidine and a metal ion such as nickel or cobalt, glutathione-S-transferase and glutathione, DNA binding protein and DNA, antibody and antigen molecules (epitopes), carmodulin and carmodulin binding peptide, ATP binding protein and ATP, estradiol receptor protein and estradiol, and various other combinations of receptor proteins and their ligands.

Among these, preferable examples of combinations of solid-phase binding sites and solid-phase binding site recognition sites include maltose binding protein and maltose, polyhistidine and a metal ion such as nickel or cobalt, glutathione-S-transferase and glutathione and antibody and antigen molecules (epitopes), while the combination of polyhistidine and metal ion such as nickel or cobalt is most preferable from the viewpoint of ease of use.

Polyhistidine is preferably used in the form of a hexamer or larger. In order to contain polyhistidine in a protein or peptide, a base sequence that encodes polyhistidine is preferably added to the end of cDNA in advance by PCR and the like.

In addition, the aforementioned solid-phase binding site recognition site may be formed on the substrate based on a prescribed pattern such as a circular or rectangular pattern having a prescribed pitch, a linear pattern of a prescribed pitch, or a combination thereof. In this case, the aforementioned protein or peptide is printed in an arbitrary size and shape corresponding to the pattern of the solid-phase binding site recognition site patterned on the substrate.

Next, the aforementioned superimposed substrate 15 is separated from the aforementioned engraved plate 11 (step d). The specific opening shape possessed by the aforementioned microscopic grooves 12 is reflected as is in the shape of the spots on the aforementioned substrate 15. Moreover, the spots on the aforementioned substrate 15 are printed without altering positional information of the corresponding DNA 13 immobilized on the engraved plate 11.

The substrate 15 on which protein or peptide 17 has been immobilized in this manner is then washed with PBS and the like to produce the protein array or peptide array 18 (step e).

Second Embodiment

Figure 3A:
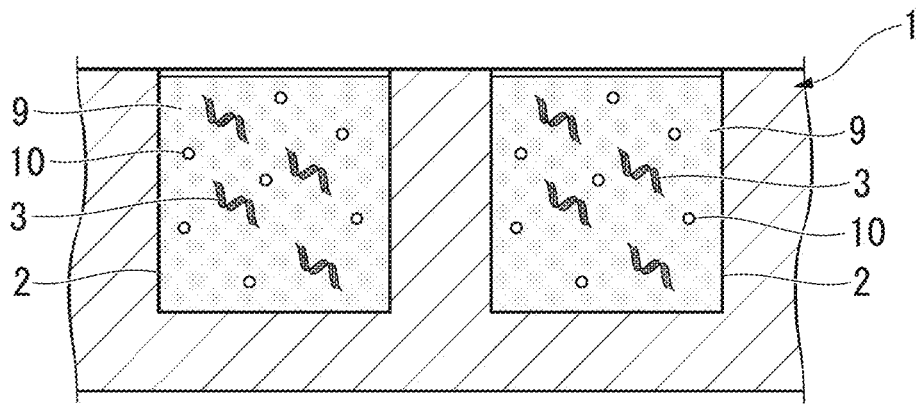
FIG. 3A is a schematic diagram of a protein or peptide printing method in the present embodiment.
Figure 3B:
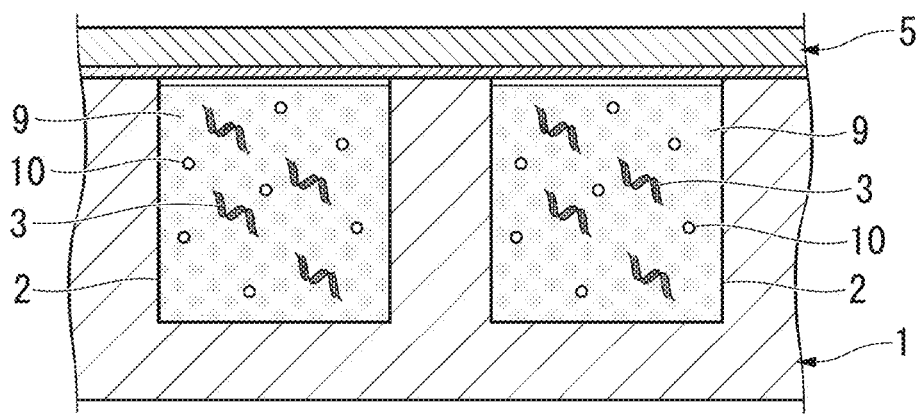
FIG. 3B is a schematic diagram of a protein or peptide printing method in the present embodiment.
Figure 3C:
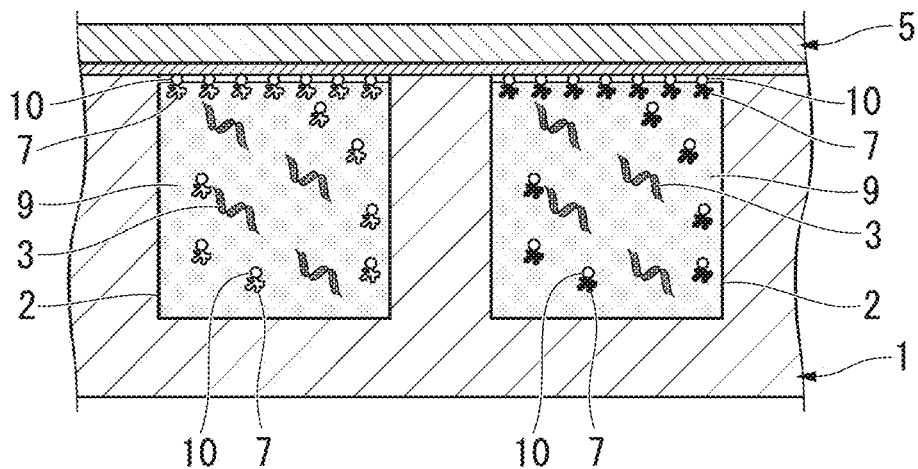
FIG. 3C is a schematic diagram of a protein or peptide printing method in the present embodiment.
Figure 4A:
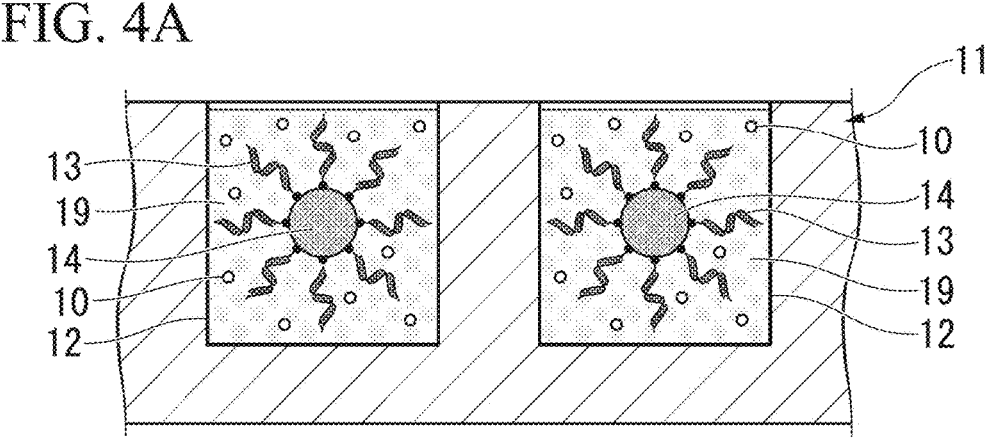
FIG. 4A is a schematic diagram of a protein or peptide printing method in the present embodiment.
Figure 4B:
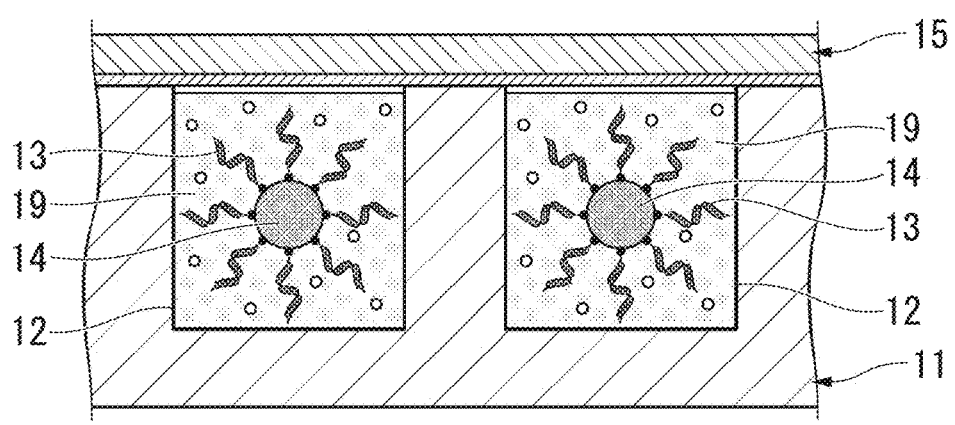
FIG. 4B is a schematic diagram of a protein or peptide printing method in the present embodiment.
Figure 4C:
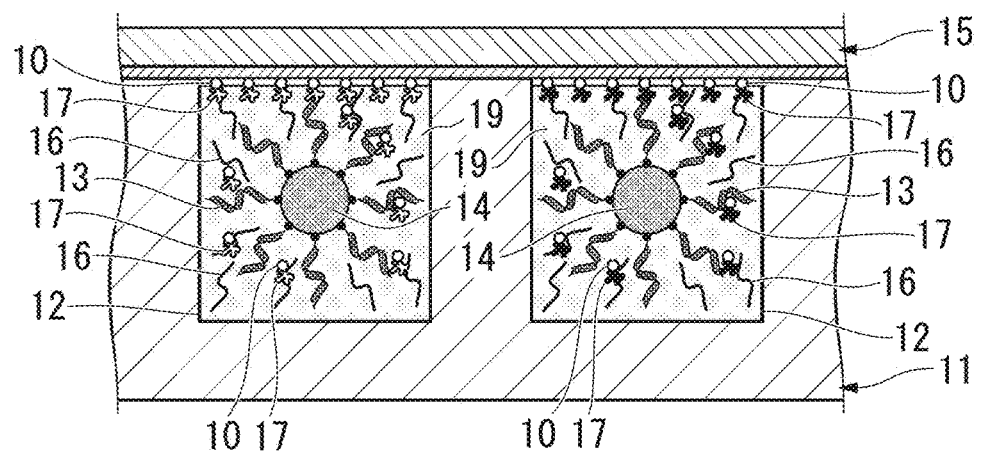
FIG. 4C is a schematic diagram of a protein or peptide printing method in the present embodiment.
Figure 4D:
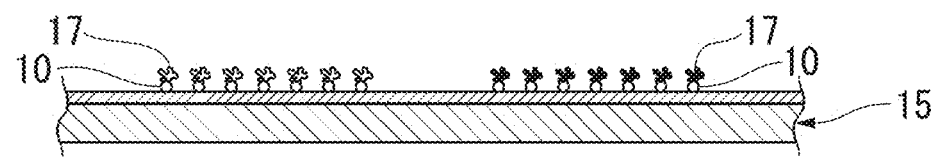
FIG. 4D is a schematic diagram of a protein or peptide printing method in the present embodiment.
Figure 4E:
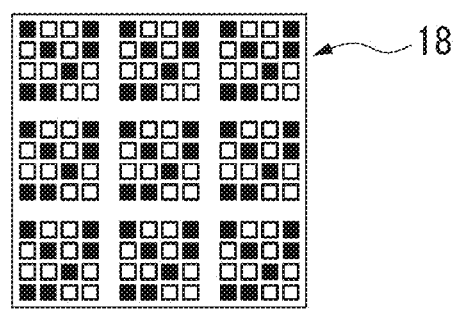
FIG. 4E is a schematic diagram of a protein or peptide printing method in the present embodiment.

As shown in FIGS. 3A to 3C, the protein or peptide printing method of the present embodiment comprises:

(a) a step for preparing the nucleic acids 3, a biotinylated puromycin derivative 10 and the acellular protein synthesis system 9 in the engraved plate 1 composed of the microscopic grooves 2 having a specific opening shape, (b) a step for superimposing the avidin-labeled substrate 5 on the engraved plate 1 so as to contact the protein or peptide 7 to be synthesized in the microscopic grooves 2, and (c) a step for synthesizing the protein or peptide 7 from the nucleic acids 3 using the acellular protein synthesis system 9 in the microscopic grooves 2, and immobilizing the protein or peptide 7 on the substrate 5 along the specific opening shapes of the microscopic grooves 2.

The following provides an explanation of each step with reference to FIGS. 4A to 4E. In FIGS. 4A to 4E, the same reference symbols are used to indicate those constituent features in FIGS. 4A to 4E that are the same as those indicated in the schematic drawings of the protein or peptide printing method of FIGS. 2A to 2E, and explanations thereof are omitted.

In step (a), DNA immobilized on a solid phase is preferable for the nucleic acids prepared in the microscopic grooves 12. A method using avidin-biotin binding is preferably used for immobilization, and a method consisting of immobilizing avidin on a solid phase followed by binding biotin to DNA is more preferable.

The substrate 15 used in step (b) can be labeled with avidin, and a biotinylated protein or peptide 17 can be immobilized in step (c). Here, streptavidin is preferable for the avidin used to label the substrate 15 from the viewpoint of ease of use.

In the present embodiment, the biotinylated puromycin derivative 10 refers to a biotinylated complex of puromycin and nucleotide. Puromycin is a compound having a chemical structure that resembles tRNA having an aminoacyl group on the 3'-end thereof, and has the property of binding to the C terminal of synthesized protein when protein is synthesized in a translation system. Consequently, during protein or peptide synthesis in the present embodiment, the biotinylated puromycin derivative 10 prepared in the microscopic grooves 12 binds to the C terminal of the synthesized protein or peptide 17 in step (a).

In the present embodiment, the aforementioned biotinylated puromycin derivative is preferably a compound represented by the aforementioned general formula (1). In the aforementioned general formula (1), Z represents a group represented by the aforementioned formula (2), (3) or (4).

Namely, the aforementioned biotinylated puromycin derivative is preferably a derivative obtained by biotinylating deoxycitidyl puromycin, ribocytidyl puromycin or deoxyuridyl puromycin.

Moreover, in the aforementioned general formula (1), Z is preferably a group represented by the aforementioned formula (2), and the aforementioned biotinylated puromycin derivative is particularly preferably a biotinylated deoxycitidyl puromycin derivative represented by the following formula (6):

[Chemical Formula 4]

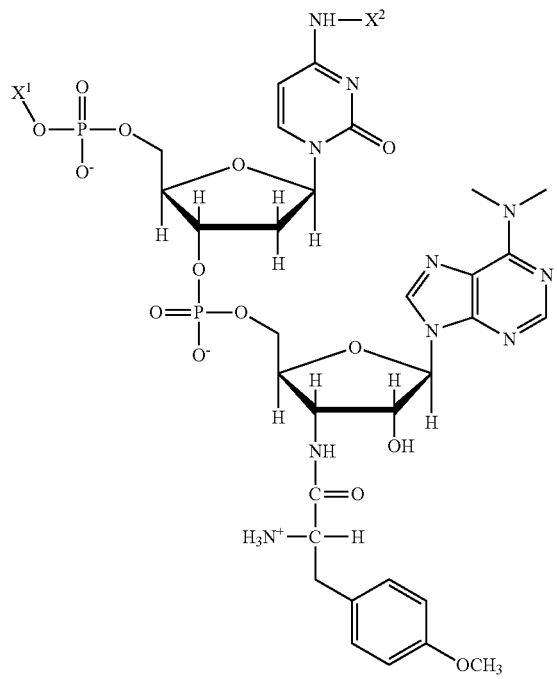

(6)

(wherein, at least one of $X^1$ and $X^2$ represents a group represented by the following formula (5), and the other is a fluorescent group or hydrogen atom:

[Chemical Formula 5]

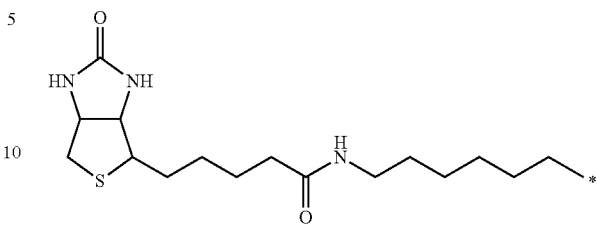

(5)

(wherein, * represents a binding site)).

In the aforementioned formulas (2) to (4) and (6), at least one of $X^1$ and $X^2$ represents a group (biotin) represented by the aforementioned formula (5). More specifically, only one of $X^1$ and $X^2$ may be biotin or both $X^1$ and $X^2$ may be biotin. As a result of the puromycin derivative having biotin, biotin is added to the C terminal of the protein or peptide 17 during synthesis thereof in step (c). Thus, in the present embodiment, it is not necessary to add a base sequence that encodes hexahistidine or other peptide or protein to the end of the cDNA used as a template.

In addition, in the case of using a mutant DNA library for the nucleic acids prepared in the microscopic grooves 12 in step (a), there are cases in which DNA is present in the mutant DNA library in which a stop codon has been introduced into the coding region thereof. In the case of synthesizing protein using such DNA as a template, a polyhistidine tag cannot be added to the C terminal if a method is used that adds a base sequence that preliminarily encodes polyhistidine on the 3'-end of DNA. On the other hand, in the present embodiment, biotin can be added to this type of truncated protein. Thus, the protein or peptide printing method of the present embodiment is preferably used in molecular evolution engineering techniques.

In the aforementioned formula (1), in the case $X^1$ or $X^2$ is not biotin, the $X^1$ or $X^2$ may be a fluorescent group or hydrogen atom. Examples of fluorescent groups include commonly used protein or peptide fluorescent dyes, such as fluorescein, rhodamine, Cy dye, Alexa® Fluor or HyLyte® Fluor. As a result of the biotinylated puromycin derivative having a fluorescent group, the amount of protein or peptide immobilized in the fabricated protein array or peptide array can be confirmed by measuring fluorescence intensity.

The concentration of the biotinylated puromycin derivative 10 based on the total amount of reaction solution added to the microscopic grooves 12 is preferably 1 μM to 100 μM and more preferably 10 μM to 50 μM. In the case the concentration is 1 μM or more, efficiency of protein biotinylation does not become excessively low, while in the case the concentration is 100 μM or less, protein expression level does not become excessively low.

Since synthesized protein is susceptible to deactivation due to decomposition or denaturation, it is necessary to maintain the protein in as stable a state as possible when printing onto a substrate. In the present embodiment, since the protein 17 synthesized in the microscopic grooves 12 is printed as is onto the substrate 15, an array 18' can be fabricated in which protein deactivation is inhibited as much as possible.

<<Protein Array or Peptide Array>>

The protein array or peptide array of the present embodiment produced using the protein or peptide printing method of the present embodiment has an arbitrary spot shape and is capable of accommodating high spot density. In addition, since the protein array or peptide array is manufactured from the aforementioned engraved plate as necessary at the time of use, denaturation and the like of protein or peptide on the array can be decreased.

<<Functional Protein or Functional Peptide Identification Method>>

The functional protein or functional peptide identification method of the present embodiment comprises carrying out functional screening using the protein array or peptide array previously described, and identifying a protein or peptide specified by the aforementioned functional screening that has been immobilized in the aforementioned step (c) by using the corresponding nucleic acids in the microscopic grooves in the aforementioned step (a).

Although the aforementioned functional screening method is dependent on a desired function possessed by a protein or peptide, the following indicates an example of the steps contained therein in the case of measuring the activity (affinity) of the protein or peptide.

First, an engraved plate is prepared so as to correspond to the locations of spots immobilized on the protein array or peptide array.

Next, a solution required for measuring activity of the protein or peptide is preliminarily filled into the microscopic grooves of the engraved plate, and protein array or peptide array is superimposed on the engraved plate and allowed to react.

The activity of a protein or peptide on an array can be measured using these steps.

A protein array or peptide array produced according to the protein or peptide printing method of the present embodiment is printed onto a substrate without altering positional information of the corresponding amino acids immobilized on the engraved plate. Accordingly, by recovering DNA in the microscopic grooves on the engraved plate corresponding to spots specified by the aforementioned functional screening using the peptide array or protein array, and then analyzing the base sequence thereof, protein having a specific function or DNA encoding that protein can be identified.

According to the functional protein or functional peptide identification method of the present embodiment, since a protein or peptide having a desired function can be rapidly identified from a high-density protein array or peptide array, this identification method is preferably used in molecular evolution engineering applications.

Although the following provides a more detailed explanation of the present invention through examples thereof, the present invention is not limited to the following examples.

Examples

Fabrication of cDNA-Bound Magnetic Beads

30 μl of streptavidin-labeled beads having a diameter of about 40 μm (approx. 300 beads) were transferred to a 1.5 ml tube, and the beads were attracted to the bottom of the tube using a magnet followed by removal of the supernatant. After washing twice using 1× binding buffer (10 mM Tris-HCl (pH 8.0), 1 mM EDTA, 1 M NaCl and 0.1% Triton X-100), 50 μl of Green Fluorescent Protein (GFP)-His-tagged cDNA labeled with biotin (40 pmol) and 50 μl of 2× binding buffer (20 mM Tris-HCl (pH 8.0), 2 mM EDTA, 2 M NaCl and 0.2% Triton X-100) were added followed by mixing by inverting for 60 minutes. After attracting the beads to the bottom of the tube using a magnet and removing the supernatant, the beads were suspended in 10 μl of PBS or TNT (trade name) reaction buffer (Promega Corp.).

(Introduction of cDNA-Bound Magnetic Beads into Intaglio Plate)

10 μl of the cDNA-bound magnetic bead suspension fabricated in the manner described above were introduced into the wells of a silica glass template (30 mm×30 mm, t=0.5) in which 100×100 microwells (diameter: 80 μm, depth: 45 μm) were arranged in the form of an array. Confirmation of whether or not the cDNA-bound magnetic beads had been introduced into the microwell mold was carried out by observing using an inverted microscope. The results are shown in FIG. 5.

Figure 5:
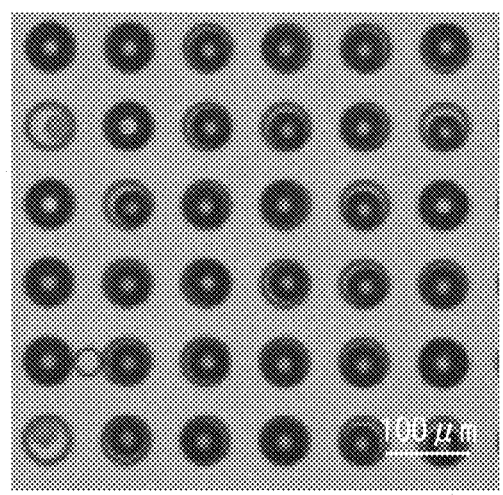
FIG. 5 is a microscopic image of an intaglio plate (an engraved plate) in which magnetic beads have been sealed in an example.

In FIG. 5, one cDNA-bound magnetic bead is introduced into each well of the intaglio plate. In this manner, the magnetic beads were confirmed to be efficiently introduced into the microwell mold.

(Patterning of GFP-His-Tagged Protein Using Glass Substrate)

After dropping in an acellular protein synthesis system solution capable of inducing transcription and translation simultaneously (TNT (trade name) Coupled Wheat Germ Extract System, Promega Corp.) into the intaglio plate into which the cDNA-bound magnetic beads had been introduced into a microwell mold, a glass plate labeled with nickel-nitriloacetic acid (Ni-NTA) was adhered to the plate and stored for about 1 hour.

Subsequently, the Ni-NTA substrate was separated from the intaglio plate and washed with PBS buffer, and whether or not GFP-His-tagged protein had been patterned on the substrate was confirmed with a fluorescence microscope (excitation wavelength: 488 nm, emission wavelength: 515 nm). The results are shown in FIG. 6.

Figure 6:
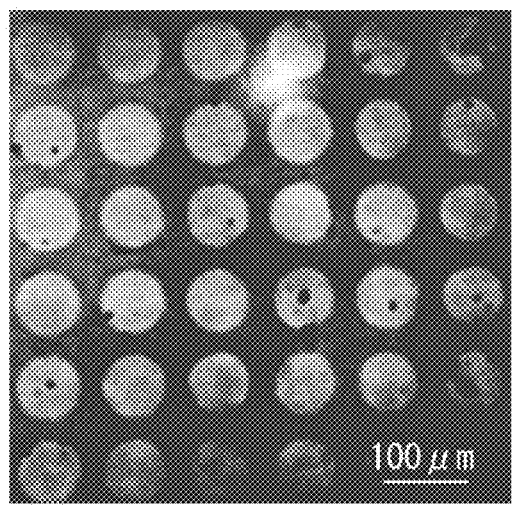
FIG. 6 is a fluorescence microscopic image of a glass substrate patterned with GFP-His-tagged protein in an example.

As shown in FIG. 6, fluorescent spots derived from GFP on the glass substrate were observed to be arranged in the form of an array. On the basis thereof, the GFP-His-tagged protein was confirmed to have been patterned on the Ni-NTA-labeled glass substrate corresponding to the intaglio plate into which the GFP-His-tagged cDNA-bound magnetic beads had been introduced.

On the basis of the above results, according to the protein or peptide printing method of the present embodiment, protein or peptide synthesis can be carried out in a microstructure in the form of a microwell mold, and the bound protein or peptide can be immobilized on a substrate surface in the form of a fine pattern. Thus, according to the protein or peptide printing method of the present embodiment, protein of an arbitrary size and shape can be printed on a substrate.

(Synthesis of Fluorescent-Labeled Biotinylated Puromycin-Nucleotide Complex) A compound represented by the aforementioned formula (6) in which $X^1$ represents Cy5 and $X^2$ represents biotin represented by the aforementioned formula (5) (to be referred to as a fluorescent-labeled biotinylated puromycin-nucleotide complex) was synthesized according to the standard phosphoramidite method. In addition, a compound in which $X^1$ represents Cy5 and $X^2$ represents a hydrogen atom (to be referred to as a fluorescent-labeled puromycin-nucleotide complex) was also fabricated for use as a control.

(Protein Synthesis Using Acellular Transcription/Translation System (Cell-Free Transcription/Translation system) and Biotinylation)

A pET21a-d(+) vector inserted with Green Fluorescent Protein (GFP) cDNA (Novagen, Inc.) was linearized using restriction enzyme.

Next, GFP cDNA containing a vector-derived T7 promoter was amplified by using the linearized vector as a template and using ExTaq DNA Polymerase (Takara Bio Inc.). The amplified fragment (PCR product) was purified using the QUAquick PCR Purification Kit (Qiagen Corp.) and used as a template for an acellular transcription/translation system (a cell-free transcription/translation system).

Next, protein was synthesized using the PureSystem (trade name) Classic II System (Biocomber Co., Ltd.) for the acellular transcription/translation system. More specifically, after mixing 5 µl (0.1 µg/µl) of the PCR product with 35 µl of the PureSystem (trade name) Classic II lysate (transcription/translation system mixture), the mixture was added in 8 µl aliquots to each well of a 384-well microtiter plate to which had been added in advance 2 µl of the fluorescent-labeled biotinylated puromycin-nucleotide complex (final concentration: 2 µM to 40 µM). The reaction was carried out under conditions of 1 hour at 37° C., and the reaction was stopped by placing the plate on ice. The reaction product was analyzed with a fluoroimager (GE Healthcare Ltd., trade name: Typhoon 9410) after carrying out SDS-PAGE using 12% gel. The results are shown in FIG. 7.

Figure 7:
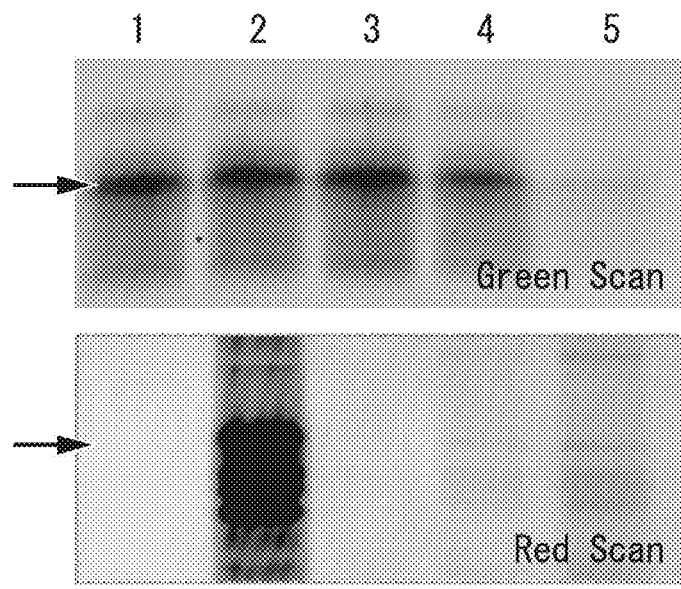
FIG. 7 shows the results of SDS-PAGE in an example.

In FIG. 7, lane 1 indicates a GFP expression sample in the case of not adding the fluorescent-labeled biotinylated puromycin-nucleotide complex or fluorescent-labeled puromycin-nucleotide complex, lane 2 indicates a GFP expression sample in the case of having added the fluorescent-labeled puromycin-nucleotide complex at 10 µM, lane 3 indicates a GFP expression sample in the case of having added the fluorescent-labeled biotinylated puromycin-nucleotide complex at 2 µM, lane 4 indicates a GFP expression sample in the case of having added the fluorescent-labeled biotinylated puromycin-nucleotide complex at 10 µM, and lane 5 indicates a GFP expression sample in the case of having added the fluorescent-labeled biotinylated puromycin-nucleotide complex at 40 µM, and the arrows indicate the target protein in the form of GFP. The electrophoresis results shown in the upper and lower rows indicate the results of analyzing using different imaging methods for the same gel. The upper row (Green Scan) indicates the results of acquiring fluorescent images with GFP, while the lower row (Red Scan) indicates the results of acquiring fluorescent images with Cy5.

Expression of GFP was confirmed in the upper lanes 3 to 5. In addition, expression of biotinylated GFP incorporating the fluorescent-labeled biotinylated puromycin-nucleotide complex was confirmed in the lower lanes 3 to 5.

Moreover, in the upper lanes 4 and 5, fluorescence intensity derived from GFP was more strongly detected in lane 4. On the other hand, in the lower lanes 4 and 5, Cy5 fluorescence intensity was more strongly detected in lane 5. On the basis of these results, the sample to which had been added the fluorescent-labeled biotinylated puromycin-nucleotide complex at 40 µM was confirmed to demonstrate particularly high biotinylation efficiency.

(Patterning of Biotinylated GFP Protein Using Slide Glass)

PBS (pH 7.5) containing 20 µg of streptavidin and 10% glycerol was dropped onto a slide glass coated with biotin (Micro Surface Corp., trade name: Bio-02) to fabricate a slide glass coated with streptavidin. Next, GFP protein synthesis reaction solution was added to each well of a 384-well microtiter plate according to the method described in the section entitled "Protein Synthesis Using Acellular Transcription/Translation System and Biotinylation" and the slide glass coated with streptavidin was adhered thereto followed by storing in a humidification chamber for about 30 minutes at room temperature.

Subsequently, the streptavidin-coated slide glass was separated from 384-well microtiter intaglio plate and washed three times for 15 seconds each with PBS 1× washing buffer (100 mM phosphate, 150 mM NaCl and 0.05% Triton X-100). Moreover, the slide glass was rinsed with water and air-dried. Whether or not the GFP protein was patterned on the slide glass was confirmed by observing fluorescence derived from GFP using a fluoroimager. The results are shown in FIG. 8.

Figure 8:
FIG. 8 is a fluorescence microscopic image of a slide glass patterned with GFP protein in an example.

In FIG. 8, the upper left spot indicates a GFP expression sample in the case of having added the fluorescent-labeled puromycin-nucleotide complex at 10 µM, the upper right spot a GFP expression sample in the case of having added the fluorescent-labeled biotinylated puromycin-nucleotide complex at 2 µM, the lower left spot indicates a GFP expression sample in the case of having added the fluorescent-labeled biotinylated puromycin-nucleotide complex at 10 µM, and the lower right spot indicates a GFP expression sample in the case of having added the fluorescent-labeled biotinylated puromycin-nucleotide complex at 40 µM. Although fluorescence is not observed in the upper left spot, fluorescence intensity in the other spots was confirmed to have increased dependent on the concentration of the fluorescent-labeled biotinylated puromycin-nucleotide complex.

On the basis thereof, protein was confirmed to have been biotinylated and be easily patterned on the substrate by adding the biotinylated puromycin-nucleotide complex to a protein synthesis system.

On the basis of the above results, according to the protein or peptide printing method of the present embodiment, biotinylated protein or biotinylated peptide can be synthesized in a microstructure in the form of a microwell mold, and the synthesized biotinylated protein or biotinylated peptide can be immobilized on a substrate surface labeled with avidin in the form of a fine pattern. Thus, according to the protein or peptide printing method of the present embodiment, protein of an arbitrary size and shape can be easily and efficiently printed on a substrate.

Moreover, since the protein array or peptide array of the present embodiment is easily and efficiently produced using the protein or peptide printing method of the present embodiment as described above, it is able to flexibly accommodate analysis of single nucleotide polymorphisms (SNP) of genes involved in lifestyle diseases or cancer and the like recently diagnosed at the genetic level as well as genes of pathogenic bacteria and viruses. According to the protein array or peptide array of the present embodiment, diagnosis of these single nucleotide polymorphisms can be made rapidly and in detail at the protein level.

INDUSTRIAL APPLICABILITY

The present invention can be used in the field of analysis of single nucleotide polymorphisms in genes involved in lifestyle diseases, cancer and the like as well as genes of pathogenic bacteria and viruses.

BRIEF DESCRIPTION OF THE REFERENCE SYMBOLS

1,11: engraved plate, 2,12: microscopic grooves, 3: nucleic acids, 4,14: magnetic beads, 5,15: substrate, 10: biotinylated puromycin derivative, 13: DNA, 16: mRNA, 7,17: protein or peptide, 9,19: acellular protein synthesis system, 18,18': protein array or peptide array

The invention claimed is:

1. A protein or peptide printing method, comprising:
   (a) preparing a mixture of a plurality of types of DNA, diluting the mixture to be dispensed so that there is 0 or 1 DNA molecule contained in each of microscopic grooves having a specific opening shape on an engraved plate, amplifying the DNA in each of the microscopic grooves, and adding a cell-free protein synthesis system, and a biotinylated complex of puromycin and nucleotide to each of the microscopic grooves,
   (b) superimposing an avidin-labeled substrate on the engraved plate so as to contact a protein or peptide to be synthesized in the microscopic grooves, and
   (c) synthesizing the protein or peptide from the nucleic acids using the cell-free protein synthesis system in the microscopic grooves, and immobilizing the protein or peptide on the substrate along the specific opening shapes of the microscopic grooves.

2. The protein or peptide printing method according to claim 1, wherein the biotinylated puromycin derivative is a compound represented by the following general formula (1):

[Chemical Formula 1]

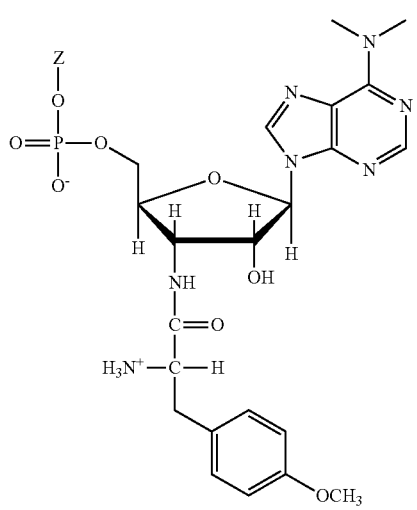

(1)

(wherein, Z represents a group represented by the following formula (2), (3) or (4):

[Chemical Formula 2]

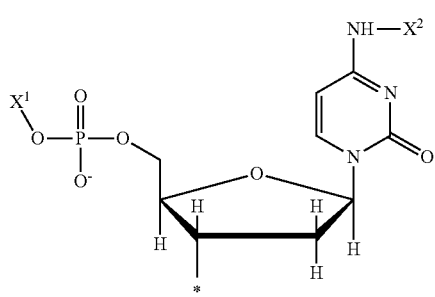

(2)

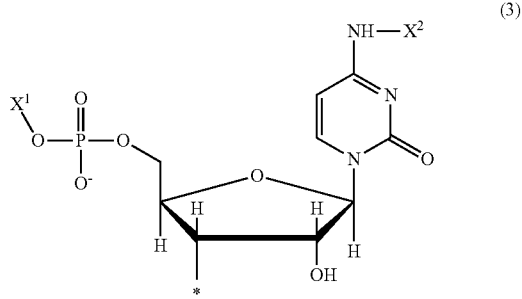

(3)

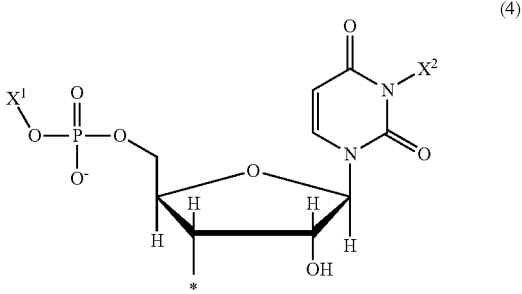

(4)

(wherein, at least one of $X^1$ and $X^2$ represents a group represented by the following formula (5), and the other is a fluorescent group or hydrogen atom, and * represents a binding site:

[Chemical Formula 3]

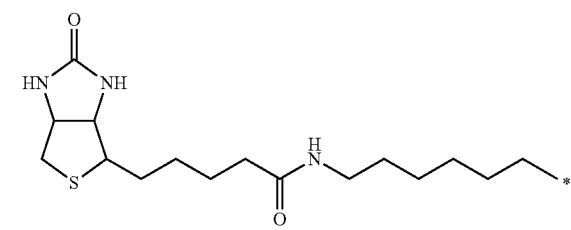

(5)

(wherein, * represents a binding site))).

3. The protein or peptide printing method according to claim 2, wherein Z is a group represented by the formula (2).

4. The protein or peptide printing method according to claim 1, wherein the cell-free protein synthesis system consists of independently purified factors required for protein synthesis.

5. A protein or peptide printing method, comprising:
   (a) preparing a mixture of: a plurality of types of DNA beads in each of which a single type DNA is immobilized on the beads through avidin-biotin or streptavidin-biotin binding, a cell-free protein synthesis system, a biotinylated complex of puromycin and nucleotide, in an engraved plate composed of microscopic grooves having a specific opening shape, a diameter of the microscopic grooves being 1 to 2 times a diameter of the beads, and a depth of the microscopic grooves being 1 to 2 times a diameter of the beads,
   (b) superimposing an avidin-labeled substrate or a streptavidin-labeled substrate on the engraved plate so as to contact a protein or peptide to be synthesized in the microscopic grooves, and (c) synthesizing the protein or peptide from the DNA using the cell-free protein synthesis system in the microscopic grooves, and immobilizing the protein or peptide on the avidin-labeled substrate or the streptavidin-labeled substrate along the specific opening shapes of the microscopic grooves.

6. The protein or peptide printing method according to claim 5, wherein, in (a), the DNA is labeled with biotin, and are immobilized by magnetic beads that have been labeled with streptavidin.

7. A functional protein or functional peptide screening method, comprising:
(a) preparing a mixture of: a plurality of types of DNA beads in each of which a single type DNA is immobilized on the beads, and a cell-free protein synthesis system, in an engraved plate composed of microscopic grooves having a specific opening shape, a diameter of the microscopic grooves being 1 to 2 times a diameter of the beads, and a depth of the microscopic grooves being 1 to 2 times a diameter of the beads,
(b) superimposing a substrate on the engraved plate so as to contact a protein or peptide to be synthesized in the microscopic grooves,
(c) synthesizing the protein or peptide from the DNA using the cell-free protein synthesis system in the microscopic grooves, and immobilizing the protein or peptide on the substrate, thereby manufacturing a protein or peptide array, and
(d) carrying out functional screening using the protein or peptide array.

8. A method of manufacturing a set of protein array or a peptide array and an engraved plate, the method comprising:
providing the engraved plate having a plurality of microscopic grooves thereon and a substrate to be superimposed to the engraved plate; and
performing the protein or peptide printing method according to claim 1.

9. The functional protein or functional peptide screening method according to claim 7,
wherein, the functional screening in (d) is measuring the activity of the protein or the peptide immobilized on the substrate.

10. The functional protein or functional peptide screening method according to claim 9, further comprising
(e) performing a nucleotide sequence analysis on the DNA corresponding to the protein or peptide of which the activity is measured, thereby identifying the functional protein or the functional peptide.

* * * * *